United States Patent
Corbett

(10) Patent No.: US 10,449,275 B2
(45) Date of Patent: *Oct. 22, 2019

(54) ANATOMIC FIT OF A PERCUTANEOUS VAD FOR RIGHT HEART SUPPORT

(71) Applicant: Abiomed, Inc., Danvers, MA (US)

(72) Inventor: Scott C. Corbett, Beverly, MA (US)

(73) Assignee: ABIOMED, INC., Danvers, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/729,263

(22) Filed: Oct. 10, 2017

(65) Prior Publication Data

US 2018/0093025 A1    Apr. 5, 2018

Related U.S. Application Data

(63) Continuation of application No. 14/673,442, filed on Mar. 30, 2015, now Pat. No. 9,814,813, which is a
(Continued)

(51) Int. Cl.
*A61M 1/10* (2006.01)
*A61M 1/12* (2006.01)
(Continued)

(52) U.S. Cl.
CPC ............ *A61M 1/1008* (2014.02); *A61M 1/10* (2013.01); *A61M 1/122* (2014.02); *A61M 1/125* (2014.02); *A61M 1/3659* (2014.02); *G06F 17/5086* (2013.01); *G16H 40/40* (2018.01); *A61B 2034/107* (2016.02); *A61B 2034/108* (2016.02); *A61L 2400/16* (2013.01); *A61M 1/101* (2013.01); *A61M 2205/0216* (2013.01); *A61M 2205/0266* (2013.01); *A61M 2207/00* (2013.01); *Y10T 29/49* (2015.01)

(58) Field of Classification Search
CPC .. A61M 1/10; A61M 1/12; A61M 1/36; G06F 19/00; G06F 17/50
USPC .......................................................... 600/16
See application file for complete search history.

(56) References Cited

U.S. PATENT DOCUMENTS

| | | |
|---|---|---|
| 4,985,014 A | 1/1991 | Orejola |
| 6,395,026 B1 | 5/2002 | Aboul-Hosn et al. |

(Continued)

FOREIGN PATENT DOCUMENTS

| | | |
|---|---|---|
| EP | 0916359 A1 | 5/1999 |
| EP | 1082150 A1 | 3/2001 |

(Continued)

OTHER PUBLICATIONS

Australian Examination Report for Australian Application U.S. Appl. No. 2012261630, dated Jan. 21, 2014.
(Continued)

*Primary Examiner* — Jon Eric C Morales
(74) *Attorney, Agent, or Firm* — White & Case LLP

(57) ABSTRACT

An apparatus is disclosed including: a cannula having a shape closely matched to the anatomy of the right ventricle of the human heart, where the cannula has an outflow port configured to be located proximal the pulmonary artery and an inflow port located proximal the inferior vena cava. In some embodiments, the cannula is a close fit to the anatomy of at least 90%, 95%, or more of the population.

23 Claims, 10 Drawing Sheets

Related U.S. Application Data continuation of application No. 13/376,559, filed as application No. PCT/US2011/037984 on May 25, 2011, now Pat. No. 8,992,406.

(60) Provisional application No. 61/396,344, filed on May 26, 2010.

(51) Int. Cl.
*A61M 1/36* (2006.01)
*G06F 17/50* (2006.01)
*G16H 40/40* (2018.01)
*A61B 34/10* (2016.01)

(56) References Cited

U.S. PATENT DOCUMENTS

| | | |
|---|---|---|
| 6,532,964 B2 | 3/2003 | Aboul-Hosn et al. |
| 6,544,216 B1 | 4/2003 | Sammler et al. |
| 6,726,696 B1 | 4/2004 | Houser et al. |
| 6,974,436 B1 | 12/2005 | Aboul-Hosn et al. |
| 7,022,100 B1 | 4/2006 | Aboul-Hosn et al. |
| 7,381,179 B2 | 6/2008 | Aboul-Hosn et al. |
| 7,445,592 B2 | 11/2008 | Pecor |
| 8,888,728 B2 | 11/2014 | Aboul-Hosn et al. |
| 8,992,406 B2 * | 3/2015 | Corbett .................. A61M 1/10 600/16 |
| 9,327,068 B2 | 5/2016 | Aboul-Hosn et al. |
| 9,545,468 B2 | 1/2017 | Aboul-Hosn et al. |
| 9,561,314 B2 | 2/2017 | Aboul-Hosn et al. |
| 9,597,437 B2 | 3/2017 | Aboul-Hosn et al. |
| 9,814,813 B2 * | 11/2017 | Corbett ............... A61M 1/1008 |
| 2002/0026944 A1 | 3/2002 | Aboul-Hosn et al. |
| 2002/0045795 A1 | 4/2002 | Aboul-Hosn et al. |
| 2005/0228212 A1 | 10/2005 | Aboul-Hosn et al. |
| 2005/0234288 A1 | 10/2005 | Aboul-Hosn et al. |
| 2008/0008688 A1 | 1/2008 | Stokes et al. |
| 2009/0005725 A1 | 1/2009 | Shorey |
| 2010/0087773 A1 | 4/2010 | Ferrari |
| 2012/0203056 A1 | 8/2012 | Corbett |
| 2015/0073202 A1 | 3/2015 | Aboul-Hosn et al. |
| 2015/0230921 A1 | 8/2015 | Chau et al. |
| 2015/0328459 A1 | 11/2015 | Chin et al. |
| 2016/0045651 A1 | 2/2016 | Corbett |

FOREIGN PATENT DOCUMENTS

| | | |
|---|---|---|
| JP | 2002514472 A | 5/2002 |
| JP | 2002515301 A | 5/2002 |
| WO | 9902204 A1 | 1/1999 |
| WO | 1999058170 A1 | 11/1999 |
| WO | 1999059652 A1 | 11/1999 |
| WO | 2005037345 A2 | 4/2005 |
| WO | 2010010407 A1 | 1/2010 |

OTHER PUBLICATIONS

Drummond, et al., "Three-Dimensional Birtual Anatomic Fit Study for an Implantable Periatric Ventricular Assist Device", Computatinal Science ICCS 2006 Lecture Notes in Computer Science, 3994:855-861 (2006).

European Examination Report for EPO Application Serial No. 11725255.1, dated Jul. 10, 2014.

European Search Report issued in EP App. 16 17 0029 dated Aug. 25, 2016.

PCT International Preliminary Report on Patentability for PCT/US/2011037984, dated Dec. 6, 2012.

PCT International Search Report for PCT/US2011/037984, dated Sep. 9, 2011.

\* cited by examiner

| DIMENSION | VALUE |
|---|---|
| PRIMARY ANGLE: A - B (deg) | 0 |
| PRIMARY LENGTH: A - B (mm) | 28 |
| SECONDARY BEND ANGLE: A - B - C (deg) | 63 |
| SECONDARY RADIUS: A - B - C (mm) | 25 |
| SECONDARY LENGTH: B - C (mm) | 44 |
| TERTIARY BEND ANGLE: B - C - D (deg) | -30 |
| TERTIARY RADIUS: B - C - D (mm) | 45 |
| TERTIARY LENGTH: C - D (mm) | 18+30=48 |
| QUATERNARY BEND ANGLE (IN PLANE C - D- E): C - D - E (deg) | -87 |
| QUATERNARY BEND ANGLE (TURNED 90): (PLANE A - B - C) TO (PLANE C - D - E) ALONG C - D (deg) | -33 |
| QUATERNARY RADIUS: C - D - E (mm) | 25 |
| QUATERNARY LENGTH: D - E (mm) | 56 |
| PIGTAIL ROTATION ANGLE: FROM QUATERNARY PLANE, C - D - E (deg) | -30 |

FIG. 3

| DIMENSION | AVERAGE | ST DEV |
|---|---|---|
| PRIMARY ANGLE: DIAPHRAGM TO IVC-RA: A - B (deg) | 0.00 | 0.00 |
| PRIMARY LENGTH: DIAPHRAGM TO IVC-RA: A - B (mm) | 16.88 | 4.59 |
| SECONDARY BEND ANGLE: IVC-RA TO TV (deg) | 63.31 | 7.34 |
| SECONDARY LENGTH: IVC-RA TO TV (mm) | 43.68 | 5.96 |
| TERTIARY BEND ANGLE: TV TO PV (deg) | -29.78 | 10.67 |
| TERTIARY LENGTH: TV TO PV (mm) | 48.47 | 4.96 |
| QUATERNARY BEND ANGLE (IN PLANE): PULM VALVE TO LPA: C - D - E (deg) | -87.06 | 15.92 |
| QUATERNARY BEND ANGLE (TURNED 90): PULM VALVE TO LPA: C - D - E (deg) | -33.24 | 11.70 |
| QUATERNARY LENGTH: PULM VALVE TO LPA: D - E (mm) | 71.32 | 9.82 |
| PV TO LPA (v2, mm) | 51.65 | 6.21 |

FIG. 5

ANATOMIC FIT OF A PERCUTANEOUS VAD FOR RIGHT HEART SUPPORT

CROSS-REFERENCE TO RELATED APPLICATIONS

This application is a continuation of U.S. application Ser. No. 14/673,442 filed on Mar. 30, 2015 (now U.S. Pat. No. 9,814,813) which is a continuation of Ser. No. 13/376,559 filed on Apr. 26, 2012 (now U.S. Pat. No. 8,992,406) which is a U.S. National Stage filing under 35 U.S.C. § 371 of International Application No. PCT/US2011/037984 filed on May 25, 2011, and claims the benefit of U.S. Provisional Application Ser. No. 61/396,344 filed on May 26, 2010. The specifications of each of the foregoing applications are incorporated herein by reference in their entirety.

BACKGROUND

The present disclosure relates generally to the field of ventricular assist devices. A ventricular assist device, or VAD, is a mechanical circulatory device that is used to partially or completely replace the function of a failing heart. Some VADs are intended for short term use, typically for patients recovering from heart attacks or heart surgery, while others are intended for long term use (months to years and in some cases for life), typically for patients suffering from congestive heart failure.

VADs are designed to assist either the right (RVAD) or left (LVAD) ventricle, or both at once (BiVAD). Which of these types is used depends primarily on the underlying heart disease and the pulmonary arterial resistance that determines the load on the right ventricle. In some applications a percutaneous RVAD to support the right heart must pump blood across the pulmonary valve.

SUMMARY

The inventors have realized that a cannula may be provided which closely matches the anatomy of the vast majority of patients and is suitable for use in a VAD device, e.g., an RVAD. Medical images (e.g., CT scans) of the hearts of one or more subjects may be analyzed, e.g., to determine the position of one or more anatomical landmarks. This analysis may be used to generate a cannula shape design (e.g., of the type described herein) that matches the anatomy of most patients.

In a first aspect, an apparatus is disclosed including: a cannula having a shape closely matched to the anatomy of the right ventricle of the human heart. In some embodiments, the cannula has an outflow port configured to be located proximal the pulmonary artery (PA) and an inflow port located proximal the inferior vena cava (IVC). In some embodiments, the cannula is configured to traverse the right atrium (RA), tricuspid valve (TV) and pulmonic valve (PV).

In some embodiments, the cannula includes: a primary section corresponding to the path from the diaphragm fibrous ring in the IVC to the IVC to RA transition (IVC-RA); a secondary section corresponding to the path from the IVC-RA to the TV; a tertiary section corresponding to the path from the TV to the PV; and a quaternary section corresponding to the path between the PV and the left branch of the pulmonary artery. In some embodiments, the primary section extends to the inflow port and the inflow port is configured to be located beyond the diaphragm fibrous ring of the IVC.

In some embodiments, the cannula includes: a first segment extending from a point A to a point B having the inflow port proximal point A; a second segment extending from a point B to a point C; a third segment extending from a point C to a point D; and a fourth segment extending from a point D to a point E, having the outflow port proximal point E. In some embodiments, the first, second and third segments lie substantially in a first plane containing points A, B, and C. In some embodiments, the forth segment lies substantially in a second plane containing points C, D, and E, the second plane being oriented to the first plane at an angle of about 30 degrees. In some embodiments, the first segment has a length of about 28 mm. In some embodiments, the second segment has a length of about 44 mm. In some embodiments, the third segment has a length of about 48 mm. In some embodiments, the fourth segment has a length of about 56 mm. In some embodiments, the second segment is oriented to the first segment at an angle of about 63 degrees in the first plane, with a bend radius of curvature of about 25 mm.

In some embodiments, the third segment is oriented to the first segment at an angle of about −30 in the first plane, with a bend radius of curvature of about 45 mm. In some embodiments, the forth segment is oriented to the third segment at an angle of about −87 degrees in the second plane, with a bend radius of curvature of about 25 mm.

Some embodiments include a pigtail extension extending from the end of the fourth segment at a point proximal point E, the pigtail extension lying substantially in a third plan oriented at an angle of about −30 degrees to the second plane.

In some embodiments, the cannula is formed of a biocompatible material.

In some embodiments, the cannula is formed of a substantially rigid material.

In some embodiments, the cannula is formed of an at least partially flexible material.

In some embodiments, the cannula includes a polyurethane tube reinforced with a surrounding coil of nitinol Some embodiments include a percutaneous ventricular assist device including the cannula, and including at least on pump located within the cannula.

In some embodiments, the cannula has a shape closely matched to the anatomy of at least 80% of the adult human population, at least 90% of the adult human population at least 95% of the adult human population, or more.

In another aspect, a method is disclosed including forming a cannula of the type recited above.

In another aspect, a method is disclosed including implanting an apparatus as recited above in a human heart.

In another aspect, a method including: receiving medical image data corresponding the anatomy of the right ventricle of each of a plurality of human subjects; processing the medical image data to determine landmark information indicative of the position of a plurality of anatomical landmarks; and generating a cannula design based on the landmark information. Some embodiments include fabricating a cannula based on the cannula design.

In some embodiments, processing the medical image data to determine landmark information includes: for each of the plurality of human subjects, generating information indicative of a position of the IVC, RA, TV, PV and PA.

In some embodiments, the information indicative of the position of the IVC, RA, TV, PV and PA includes: a length and an angle between the IVC and the RA; a length and an angle between the RA and the TV; a length and an angle between the TV and PV; and a length and an angle between the PV and PA.

Some embodiments include: fabricating the cannula includes fabricating the cannula having a shape closely matched to the anatomy of the right ventricle of the human heart, where the cannula has an outflow port configured to be located proximal the PA and an inflow port located proximal the IVC.

In some embodiments, the cannula is configured to traverse the right atrium (RA), tricuspid valve (TV) and pulmonic valve (PV).

In some embodiments, the cannula includes: a primary section corresponding to the path from the diaphragm fibrous ring in the IVC to the IVC to RA transition (IVC-RA); a secondary section corresponding to the path from the IVC-RA to the TV; a tertiary section corresponding to the path from the TV to the PV; and a quaternary section corresponding to the path between the PV and the left branch of the pulmonary artery.

In some embodiments, the cannula has a shape closely matched to the anatomy of at least 80%, 85%, 90%, 95% or more of the adult human population.

In another aspect, a product is disclosed including: a cannula fabricated using any method recited above.

Each of the aspects and embodiments of the invention described herein can be used alone or in combination with one another.

The aspects and embodiments will now be described with reference to the attached drawings.

BRIEF DESCRIPTION OF THE DRAWINGS

FIG. 3 is a table showing a summary of design parameters for a cannula.

FIG. 5 illustrates the results of a right ventricle cannula fit study which determined the location of anatomical landmarks.

DETAILED DESCRIPTION OF THE PREFERRED EMBODIMENTS

Figure 1:
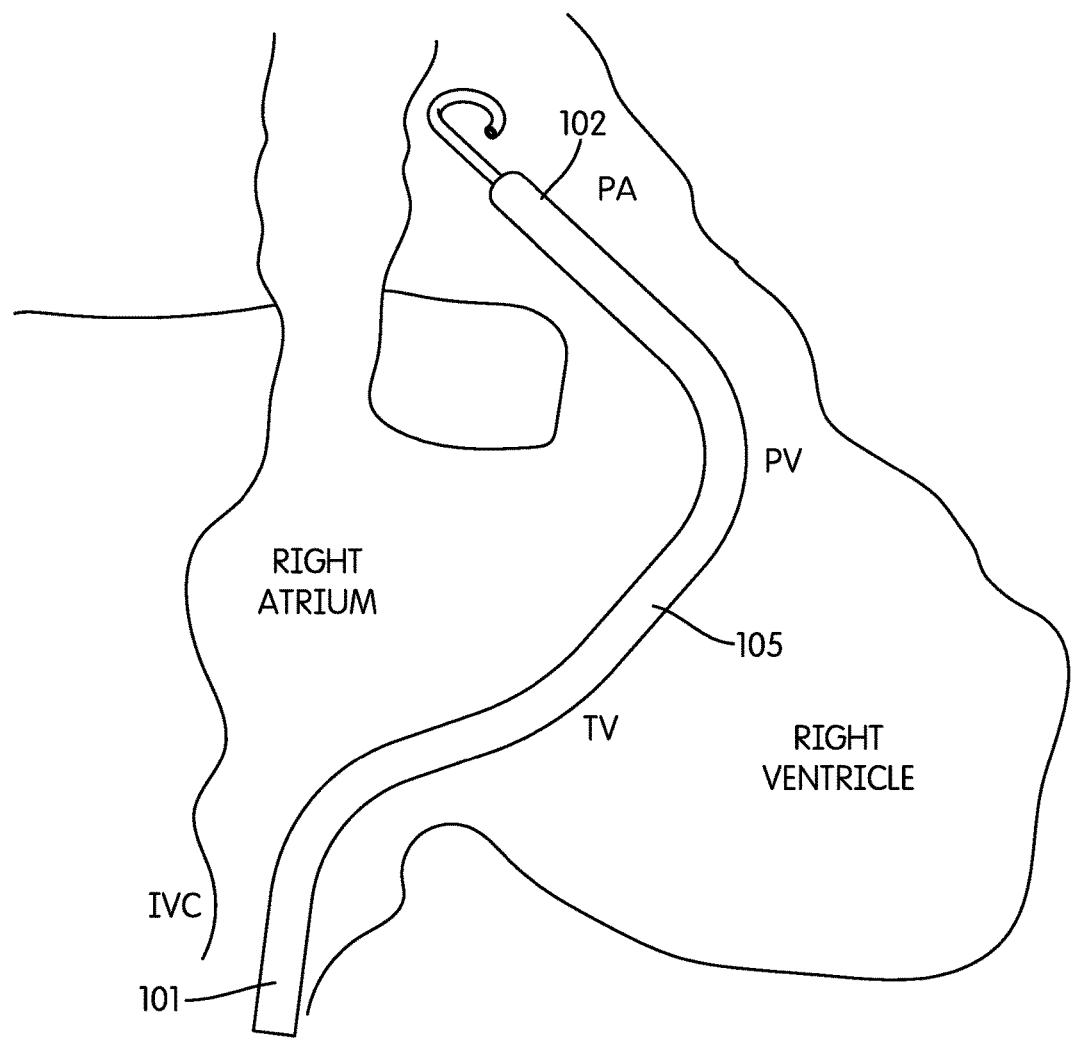
FIG. 1 shows percutaneous VAD located in the right ventricle of a heart.

Referring to FIG. 1, a catheter-based percutaneous VAD 100 for treatment of acute right heart failure is shown. As shown, the device inflow 101 resides in the inferior vena cava (IVC); a flexible cannula 105 traverses the right atrium (RA), tricuspid (TV) and pulmonic valves (PV), while the device outflow 102 resides in the pulmonary artery (PA). The cannula may house a drive system and pump, e.g., of the types used in VADs available under the Impella trade name from Abiomed, Inc of Danvers, Mass. In some embodiments, the device provides flows of up to 4 L/min or more and up to 2 weeks of support or more.

The shape of cannula 105 closely matches the anatomy of the right ventricle of the human heart. For example, as described in greater detail below, the shape of the cannula may be based on a fit study of a population of subjects, e.g., using a library of medical images (e.g., CT or MRI scan images) of the subjects. In some embodiments, the cannula is a close fit to the anatomy of at least 80%, 85%, 90%, 95%, or more of a population (e.g., the adult human population, adult male human population, adult female human population, the human population for a given age range, etc.).

Figure 2A:
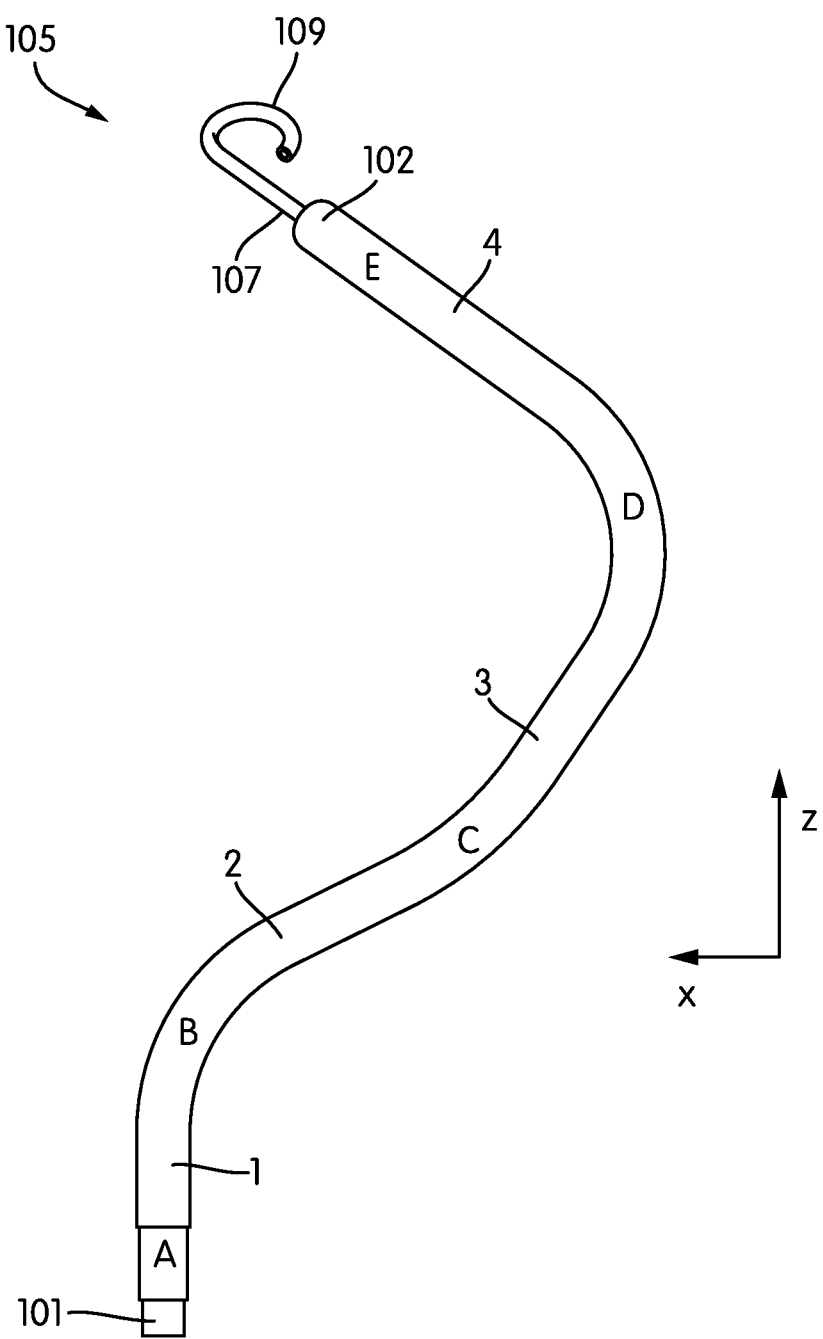
FIGS. 2A-2E each show a different perspective views of a cannula having a shape closely matched to the anatomy of the right ventricle in a broad range of subjects. For each figure, a Cartesian coordinate (x,y,z) key indicates the viewing direction.
Figure 2B:
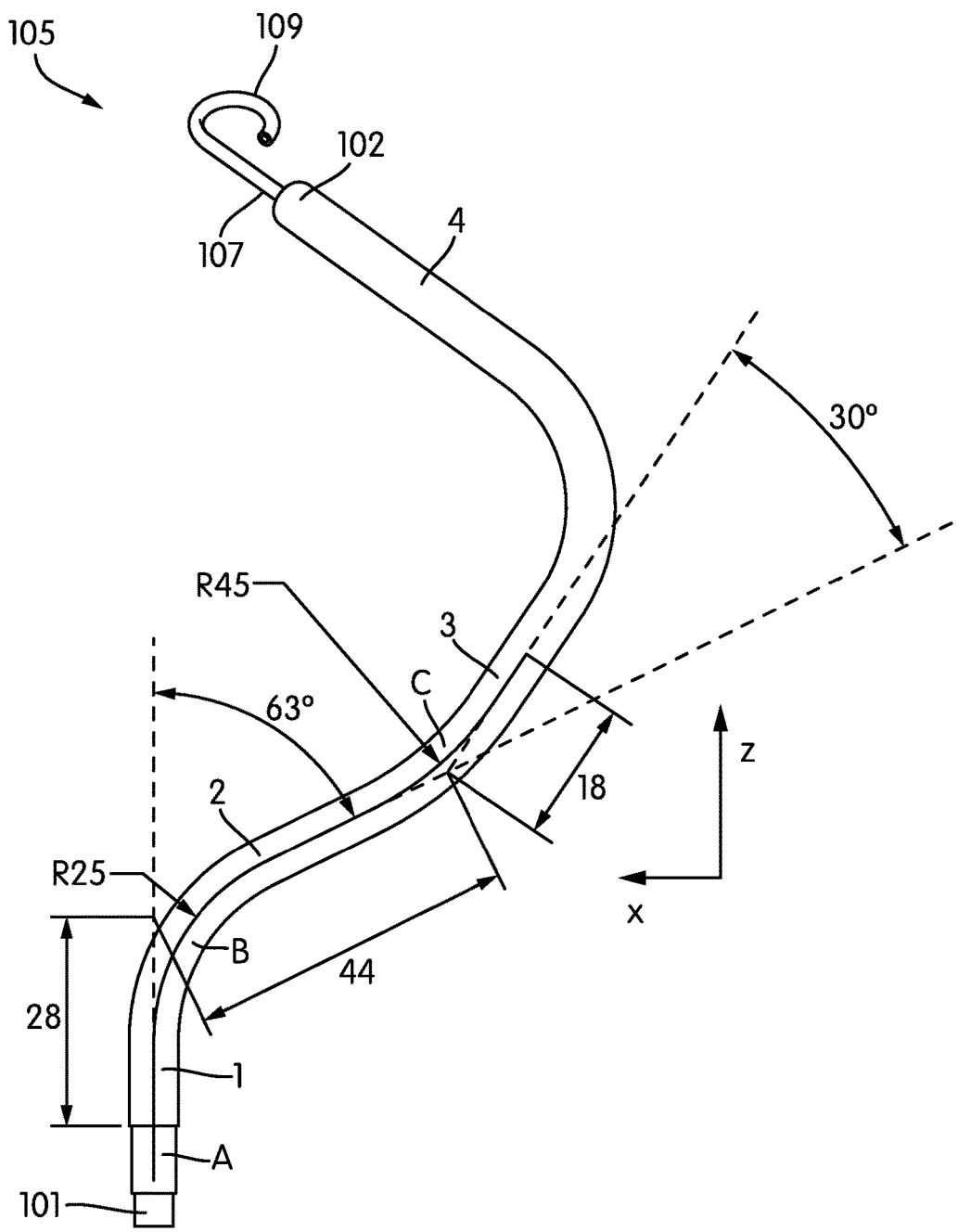
Figure 2C:
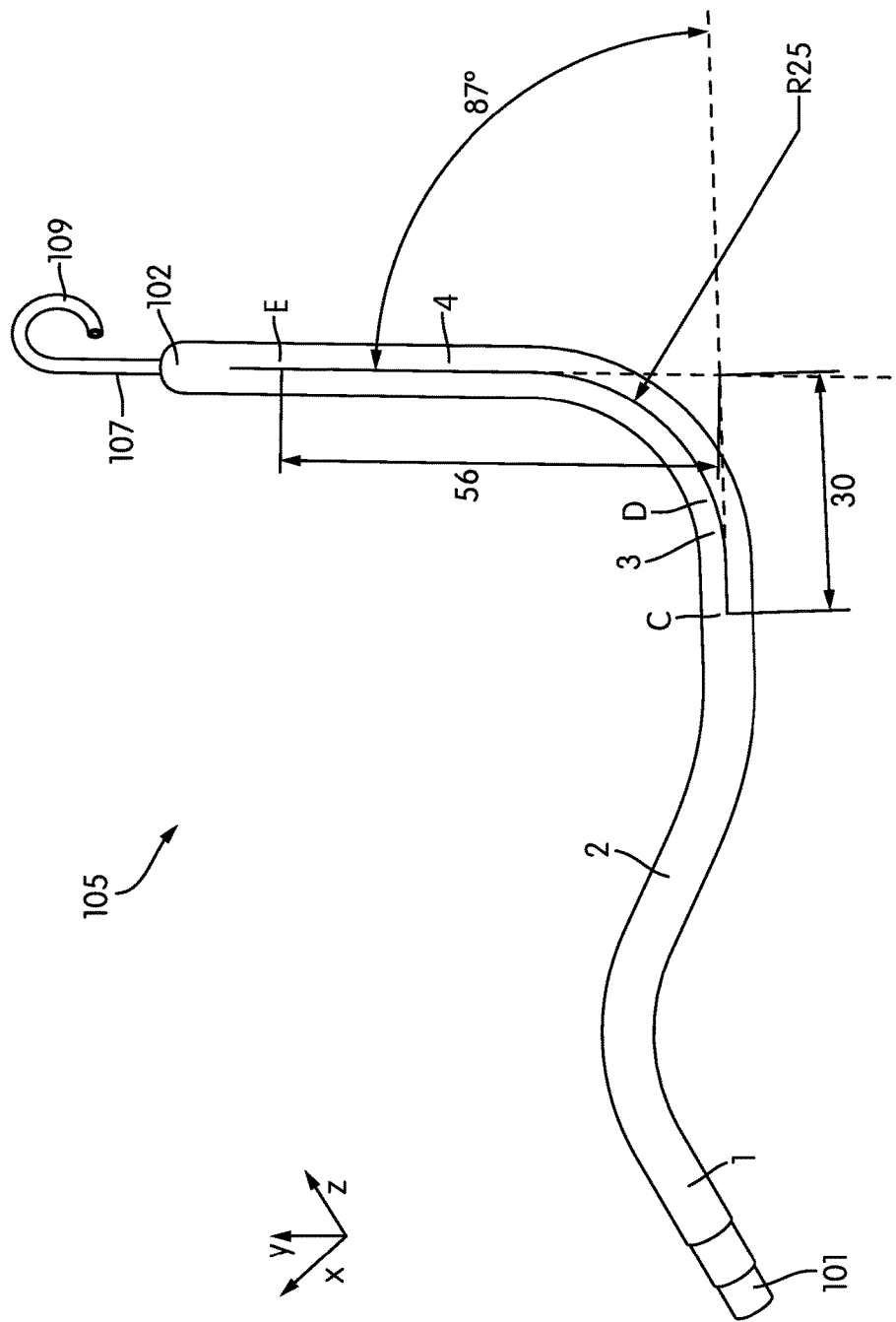

FIGS. 2A-2E show several perspective views of an embodiment of the RVAD cannula 105. As shown in FIG. 2A, the cannula extends between the inflow port 101 and the outflow port 102 and includes primary, secondary, tertiary, and quaternary sections labeled 1, 2, 3, and 4, respectively.

Beginning at the inflow port 101, the cannula 105 includes a substantially straight 28 mm primary section 1 extending between points A and B. The cannula 105 next includes a secondary section 2 extending from point B to point C. The secondary section 2 has a length of 44 mm. The angle formed between the primary and secondary sections 1, 2 is 63 degrees, with a radius of curvature of 25 mm. (See FIG. 2B.)

The secondary section 2 is followed by a tertiary section 3 extending from point C to point D. The tertiary section has a length of 48 mm. The angle formed between the secondary and tertiary sections is −30 degrees, with a radius of curvature of 45 mm. (See FIG. 2C.) he tertiary section 3 is followed by a quaternary section 4 extending from point D to point E. The quaternary section has a length of 56 mm. The angle formed between the tertiary and quaternary sections in the plane defined by points C-D-E is −87 degrees, with a radius of curvature of 25 mm. (See FIG. 2C.)

Figure 2D:
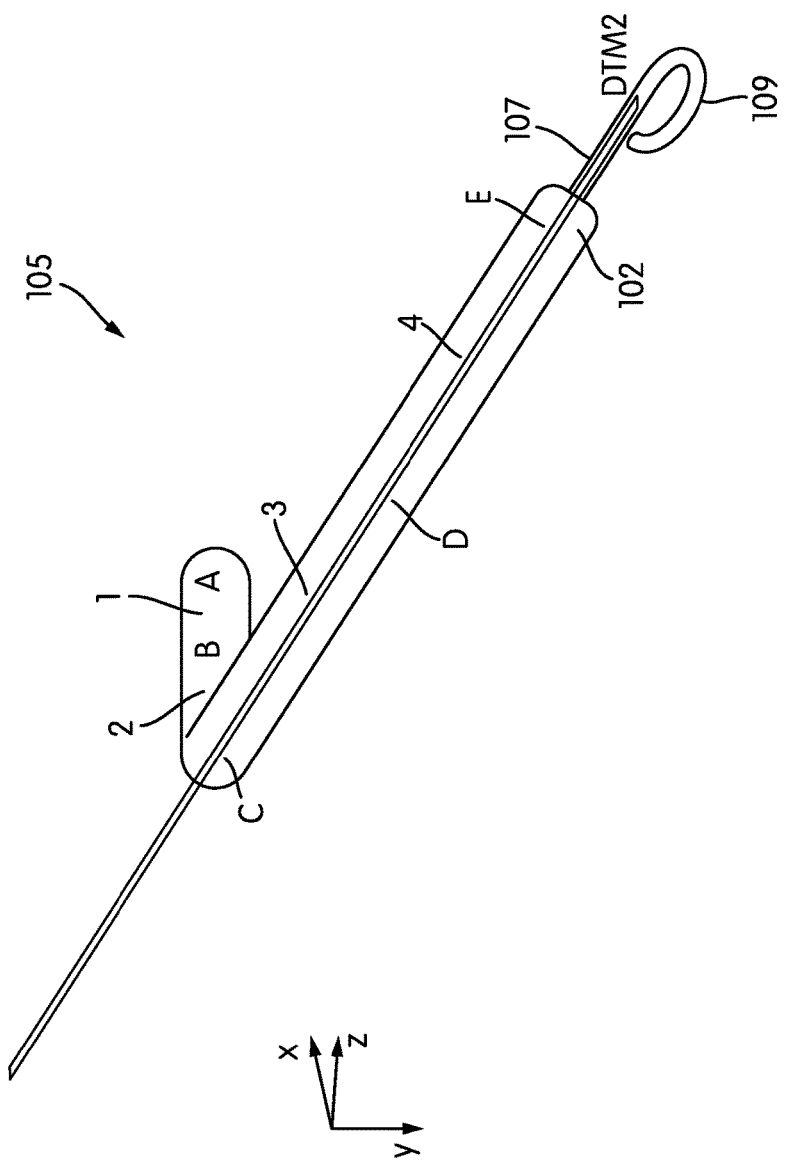

Note that the point E lies outside of the plane defined by points A-B-C. As shown in FIG. 2D, the plane defined by points A-B-C is oriented at an angle of 33 degrees to the plane define by points C-D-E.

Figure 2E:
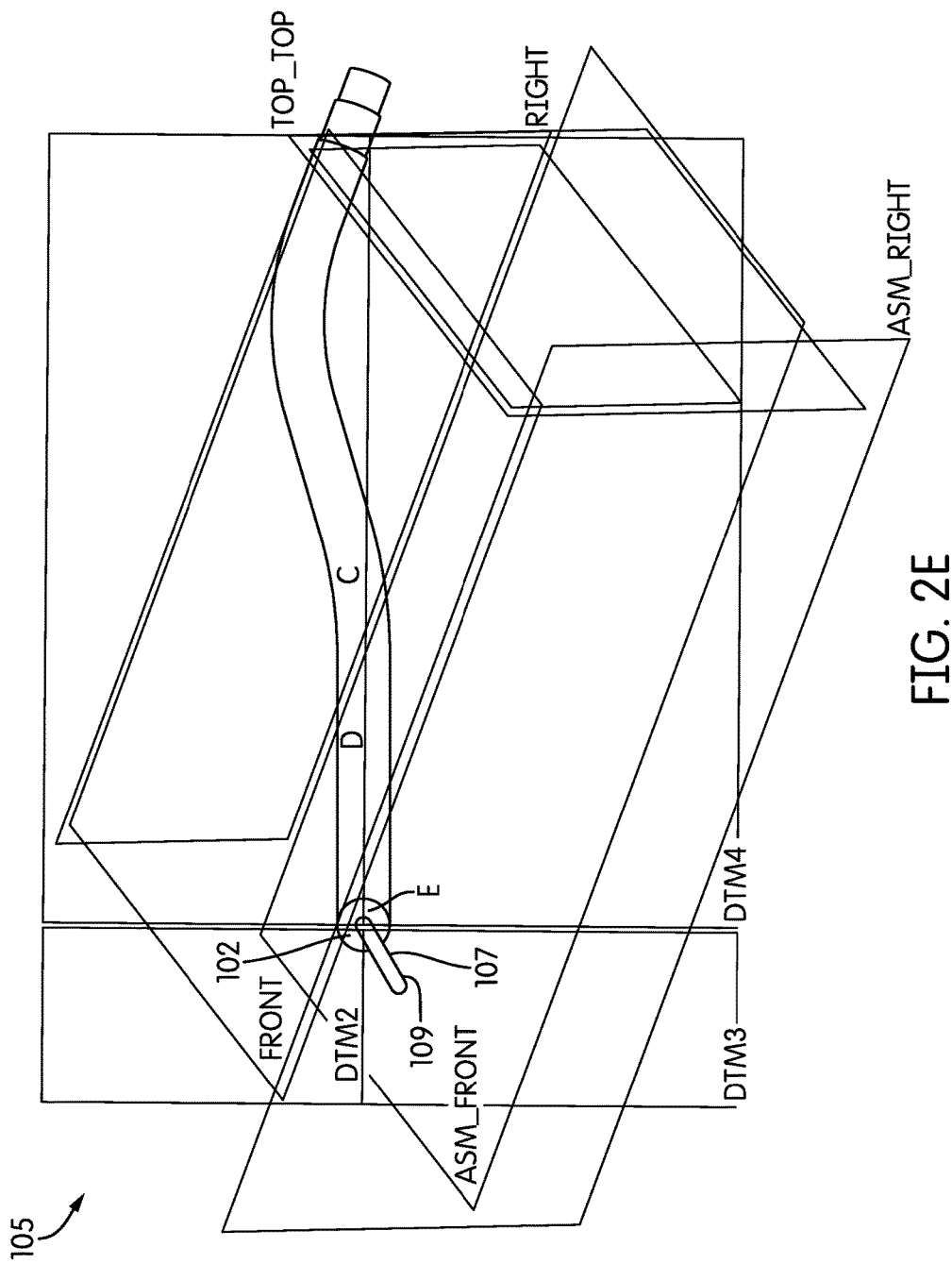

In some embodiments, contiguous to the input port 101 of the cannula 105 is an extension 107 (e.g. of soft elastic material) that mechanically, yet not hydraulically extends the cannula 13. In some embodiments, this extension 107 is provided with a pigtail tip 109 to allow for a traumatic support on body tissue. As shown in FIG. 2E, the pigtail tip 109 may be oriented at an angle of e.g., −30 degrees from the plane defined by points C-D-E.

FIG. 3 is a table summarizing the above-described dimensions of an embodiment of the RVAD cannula shown in FIGS. 2A-2E. In various embodiments, the length, radius and/or angle dimensions may vary from the values given below by less that 0.1%, 1%, 2%, 3%, 4%, 5%, 10% etc.

In various embodiments, the cannula 105 has an inner diameter in the range of 5-10 mm, e.g., 6 mm and an outer diameter of 5-10 mm, e.g., 7 mm. In some embodiments, other suitable dimensions may be used. The cannula may be constructed of any suitable biocompatible material. The material may be substantially rigid or at least partially flexible. In one embodiment, the cannula is constructed of a polyurethane tube reinforced with a coil of nitinol (or other suitable material, e.g., a material featuring shape memory). In some embodiments, the polyurethane material may include the material having the trade name Desmopan 355, available from Bayer MaterialScience AG of Leverkusen, Germany.

The cannula 105 may be fabricated using any techniques know in the art including, e.g., molding, injection molding, etc.

As noted above, the cannula 105 is designed to closely match the anatomy of the right ventricle. In some embodiments, each section of the cannula is designed to extend between the expected locations of various anatomical landmarks (e.g., as determined based on the average location of these landmarks found using an anatomical fit study). For example, in the embodiments described above, the primary section 1 corresponds to the path from the diaphragm fibrous ring in the IVC to the IVC to RA transition (IVC-RA). The secondary section 2 corresponds to the path from the IVC-RA to the TV. The tertiary section 3 corresponds to the path from the TV to the PV. The quaternary section 4 corresponds to the path between the PV and the left branch of the PA. As shown, the length of the primary section 1 is chosen such that the inflow port 101 is located beyond the diaphragm fibrous ring. As shown, the length of the quaternary section 4 is chosen such that the outflow port 102 is located at the left PA bifurcation, with extension 107 residing in the left PA.

It is to be understood that, in other embodiments, any other suitable choice of landmarks may be used. To ensure a cannula shape which conforms to the anatomy of a wide range of patients, it is advantageous to select a set of landmarks having relative locations which exhibit low patient-to-patient variability do not depend strongly on the size of the patient (e.g., as determined by the patients body surface area (BSA)). As discussed in greater detail below, the landmarks described above meet both of these criteria.

In various embodiments, the RVAD device 100 includes the cannula 105 described above enclosing one or more pumps and pump motor drives (not shown). Any suitable pump and/or drive known in the art may be used. In some embodiments, the cannula may be a component of a BiVAD device.

In some embodiments the RVAD is advantageously small, with a low blood-wetted surface area, e.g., of 100 cm$^2$ or less, 75 cm$^2$ or less, 50 cm$^2$ or less, 25 cm$^2$ or less, 10 cm$^2$ or less, etc. (e.g., in the range of 10-100 cm$^2$).

In some embodiments the cannula may be introduced into the ventricle using a catheter based technique, e.g., of the types described in Cannula Systems and Methods of Use, U.S. Pat. Pub. No. 20070066943 filed Mar. 22, 2007, the entire contents of which is incorporated herein by reference.

Figure 4:
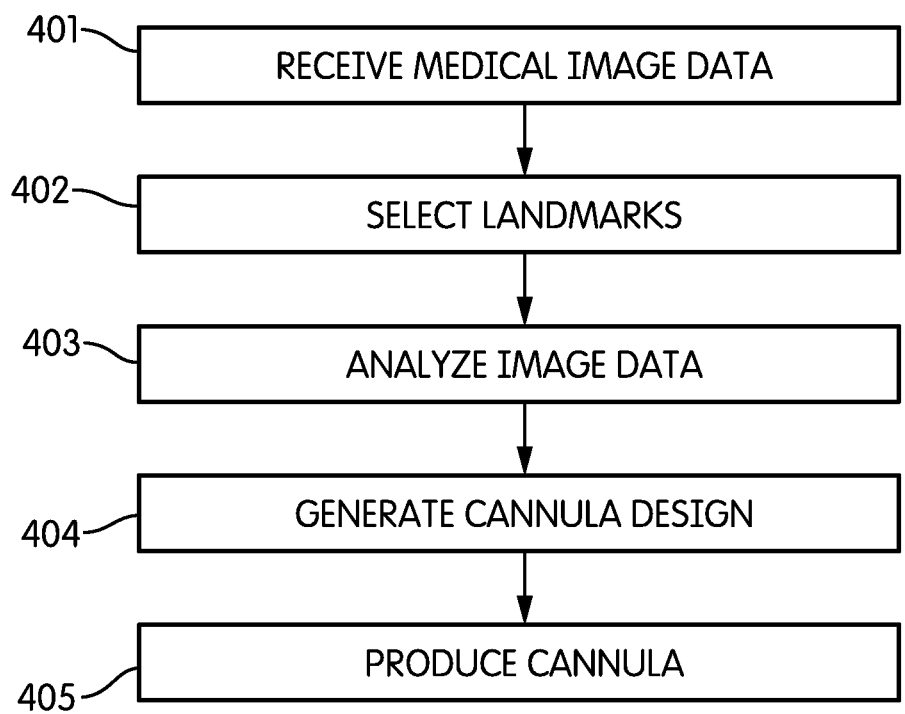
FIG. 4 illustrates a process for designing a cannula.

FIG. 4 illustrates a process 400 for designing and producing a cannula of the type described herein. In step 401, medical image data (e.g., including 3D CT or MRI scans of the hearts of a set of patients) is received or obtained (e.g., from a database).

In step 402, a set of anatomical landmarks is selected (e.g., the landmarks described with reference to FIGS. 2A-2E above). To ensure a cannula shape which conforms to the anatomy of a wide range of patients, it is advantageous to select a set of landmarks having relative locations which exhibit low patient-to-patient variability do not depend strongly on the size of the patient (e.g., as determined by the patients body surface area (BSA)).

In step 403, the image data is analyzed to locate the anatomical landmarks and determine information about their relative (and/or absolute) positions. The landmarks may be identified automatically (using any image processing or machine vision techniques known in the art), manually (e.g., by presenting the images to a medical practitioner for examination), or combinations thereof. Average positions for the landmarks may be determined over a sample population of patients In step 404, a cannula design is generated based on the analysis performed in step 404. For example, the size and/or orientations of various sections of the cannula may be determined based on the average positions for the landmarks over a sample population of patients, in order to provide a cannula design which closely matches the anatomy of the heart over a large range of patients. The cannula design may be output (e.g., as a data file containing a listing a parameters, a computer aided design (CAD) file, etc.).

In step 405, the cannula is produced based on the cannula design generated in step 404. As described above, the cannula may be fabricated using any suitable technique know in the art.

Example—RVAD Cannula Design

The following sets for one non-limiting example of a cannula design.

Nineteen representative 3D CT scans of the hearts of patients having BSA ranging from 1.5-2.6 m$^2$ were used to optimize cannula geometry using the techniques described herein. Lengths and angles between the IVC, RA, TV, PV and PA were measured using Mimics software (available from Materialise NV, Belgium).

Figure 6:
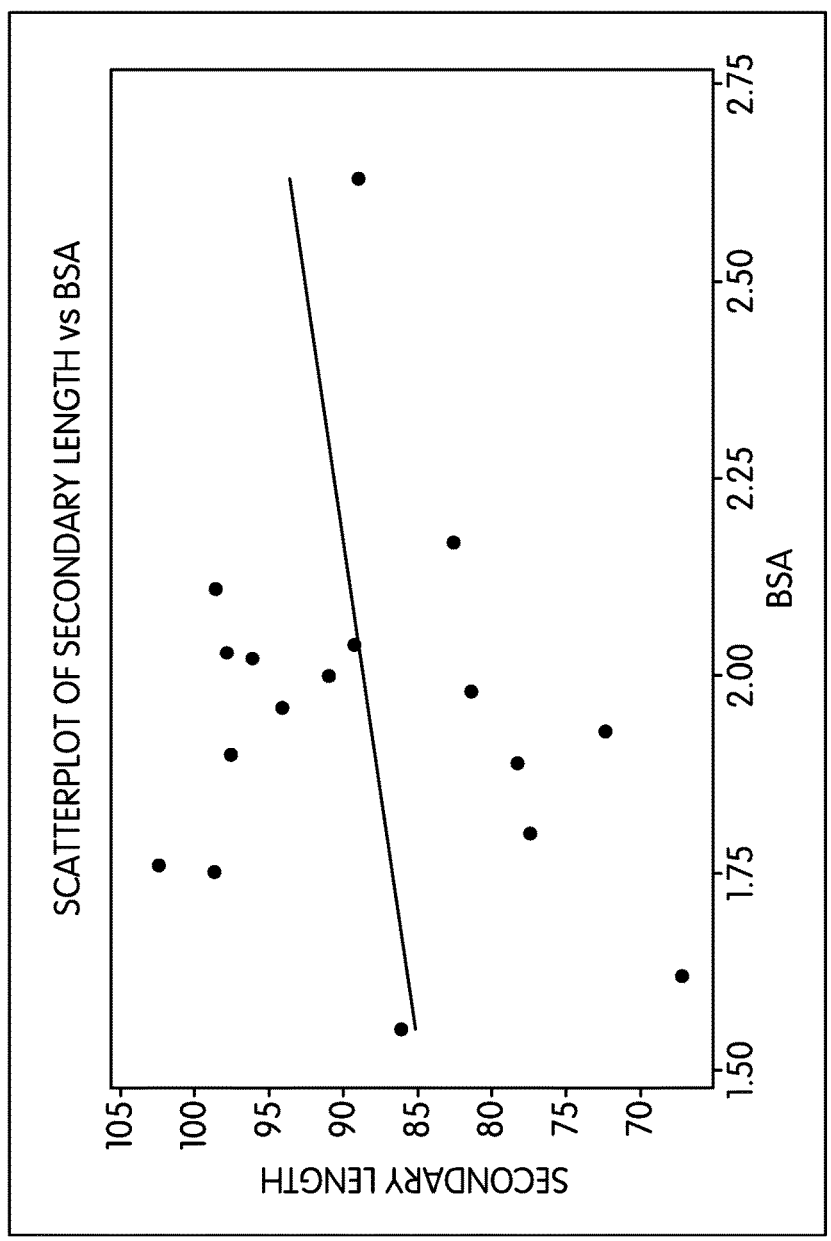
FIG. 6 is a plot of a characteristic length between anatomical landmarks in each of multiple subjects as a function the respective subject body surface area.

The results of the study are summarized in FIG. 5. Standard deviations for the length and angles were 6.3 mm and 11.4 degrees, showing low patient-to-patient variability. Further, as shown in FIG. 6, no correlation with BSA (body surface area) was found. Considerations were made for the out-of-plane nature of the TV, while placement of the device outflow at the L bifurcation of the PA resulted in a 3D cannula configuration, as described in detail above with reference to FIGS. 2A-2E and FIG. 3.

The optimized cannula design was found to fit in 95% or more of patients assuming a rigid cannula, and would fit as much as 100% of patients allowing for cannula flexibility. Additional cadaver fit studies were performed which validated the computational modeling.

Although several specific example have been shown of devices for used in the right ventricle in an adult human heart, it is to be understood that the devices and techniques described herein may be extended to other anatomical locales (e.g. the left ventricle) and/or to other types of subjects, e.g., non-human animal subjects.

While various inventive embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the inventive teachings is/are used. Those skilled in the art will recognize, or be able to ascertain using no more than routine experimentation, many equivalents to the specific inventive embodiments described herein. It is, therefore, to be understood that the foregoing embodiments are presented by way of example only and that, within the scope of the appended claims and equivalents thereto, inventive embodiments may be practiced otherwise than as specifically described and claimed.

Inventive embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure.

The above-described embodiments can be implemented in any of numerous ways. For example, the embodiments may be implemented using hardware, software or a combination thereof. When implemented in software, the software code can be executed on any suitable processor or collection of processors, whether provided in a single computer or distributed among multiple computers.

Further, it should be appreciated that a computer may be embodied in any of a number of forms, such as a rack-mounted computer, a desktop computer, a laptop computer, or a tablet computer. Additionally, a computer may be embedded in a device not generally regarded as a computer but with suitable processing capabilities, including a Personal Digital Assistant (PDA), a smart phone or any other suitable portable or fixed electronic device.

Also, a computer may have one or more input and output devices. These devices can be used, among other things, to present a user interface. Examples of output devices that can be used to provide a user interface include printers or display screens for visual presentation of output and speakers or other sound generating devices for audible presentation of output. Examples of input devices that can be used for a user interface include keyboards, and pointing devices, such as mice, touch pads, and digitizing tablets. As another example, a computer may receive input information through speech recognition or in other audible format.

Such computers may be interconnected by one or more networks in any suitable form, including a local area network or a wide area network, such as an enterprise network, and intelligent network (IN) or the Internet. Such networks may be based on any suitable technology and may operate according to any suitable protocol and may include wireless networks, wired networks or fiber optic networks.

A computer employed to implement at least a portion of the functionality described herein may comprise a memory, one or more processing units (also referred to herein simply as "processors"), one or more communication interfaces, one or more display units, and one or more user input devices. The memory may comprise any computer-readable media, and may store computer instructions (also referred to herein as "processor-executable instructions") for implementing the various functionalities described herein. The processing unit(s) may be used to execute the instructions. The communication interface(s) may be coupled to a wired or wireless network, bus, or other communication means and may therefore allow the computer to transmit communications to and/or receive communications from other devices. The display unit(s) may be provided, for example, to allow a user to view various information in connection with execution of the instructions. The user input device(s) may be provided, for example, to allow the user to make manual adjustments, make selections, enter data or various other information, and/or interact in any of a variety of manners with the processor during execution of the instructions.

The various methods or processes outlined herein may be coded as software that is executable on one or more processors that employ any one of a variety of operating systems or platforms. Additionally, such software may be written using any of a number of suitable programming languages and/or programming or scripting tools, and also may be compiled as executable machine language code or intermediate code that is executed on a framework or virtual machine.

In this respect, various inventive concepts may be embodied as a computer readable storage medium (or multiple computer readable storage media) (e.g., a computer memory, one or more floppy discs, compact discs, optical discs, magnetic tapes, flash memories, circuit configurations in Field Programmable Gate Arrays or other semiconductor devices, or other non-transitory medium or tangible computer storage medium) encoded with one or more programs that, when executed on one or more computers or other processors, perform methods that implement the various embodiments of the invention discussed above. The computer readable medium or media can be transportable, such that the program or programs stored thereon can be loaded onto one or more different computers or other processors to implement various aspects of the present invention as discussed above.

The terms "program" or "software" are used herein in a generic sense to refer to any type of computer code or set of computer-executable instructions that can be employed to program a computer or other processor to implement various aspects of embodiments as discussed above. Additionally, it should be appreciated that according to one aspect, one or more computer programs that when executed perform methods of the present invention need not reside on a single computer or processor, but may be distributed in a modular fashion amongst a number of different computers or processors to implement various aspects of the present invention.

Computer-executable instructions may be in many forms, such as program modules, executed by one or more computers or other devices. Generally, program modules include routines, programs, objects, components, data structures, etc. that perform particular tasks or implement particular abstract data types. Typically the functionality of the program modules may be combined or distributed as desired in various embodiments.

Also, data structures may be stored in computer-readable media in any suitable form. For simplicity of illustration, data structures may be shown to have fields that are related through location in the data structure. Such relationships may likewise be achieved by assigning storage for the fields with locations in a computer-readable medium that convey relationship between the fields. However, any suitable mechanism may be used to establish a relationship between information in fields of a data structure, including through the use of pointers, tags or other mechanisms that establish relationship between data elements.

Also, various inventive concepts may be embodied as one or more methods, of which an example has been provided. The acts performed as part of the method may be ordered in any suitable way. Accordingly, embodiments may be constructed in which acts are performed in an order different than illustrated, which may include performing some acts simultaneously, even though shown as sequential acts in illustrative embodiments.

All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

The foregoing detailed description has described only a few of the many forms that this invention can take. For this reason, this detailed description is intended by way of illustration, and not by way of limitation.

What is claimed is:

1. An apparatus comprising:
a cannula comprising a shape memory material configured to provide the cannula with a shape closely matched to the anatomy of the right ventricle of the human heart, wherein the cannula has:
an outflow port configured to be located proximal the pulmonary artery (PA);
an inflow port configured to be located proximal the inferior vena cava (IVC);
a primary section corresponding to the path from a diaphragm fibrous ring in the IVC to the IVC to right atrium (RA) transition (IVC-RA), extending in a first direction;
a secondary section corresponding to the path from the IVC-RA to the tricuspid valve (TV), extending in a second direction different to the first direction;
a tertiary section corresponding to the path from the TV to the pulmonary valve (PV), extending in a third direction different from the first and second directions; and
a quaternary section corresponding to the path between the PV and the left branch of the PA, extending in a fourth direction, different from the first, second and third directions,
wherein:
the primary section extends from a point A to a point B and includes the inflow port proximal point A;
the secondary section extends from said point B to a point C;
the tertiary section extends from said point C to a point D; and
the quaternary section extends from said point D to a point E, having the outflow port proximal said point E;
wherein:
the primary, secondary and tertiary sections lie substantially in a first plane containing said points A, B, and C; and
the quaternary section lies substantially in a second plane containing points C, D, and E, the second plane being oriented to the first plane at an angle of about 30 degrees.

2. The apparatus of claim 1, wherein the primary section extends to the inflow port and the inflow port is configured to be located in the IVC, beyond the diaphragm fibrous ring of the IVC.

3. The apparatus of claim 1, wherein:
the primary section has a length of about 28 mm;
the secondary section has a length of about 44 mm;
the tertiary section has a length of about 48 mm;
the quaternary section has a length of about 56 mm;
the secondary section is oriented to the first segment at an angle of about 63 degrees in the first plane, with a bend radius of curvature of about 25 mm;
the tertiary section is oriented to the first segment at an angle of about −30 degrees in the first plane, with a bend radius of curvature of about 45 mm;
the quaternary section is oriented to the third segment at an angle of about −87 degrees in the second plane, with a bend radius of curvature of about 25 mm.

4. The apparatus of claim 1, wherein the cannula is formed of a biocompatible material.

5. The apparatus of claim 4, further comprising an extension extending from the end of the quaternary section at a point proximal point E, the extension lying substantially in a third plane oriented at an angle of about −30 degrees to the second plane.

6. The apparatus of claim 1, wherein the cannula is formed of a substantially rigid material.

7. The apparatus of claim 1, wherein the cannula is formed of an at least partially flexible substantially rigid material.

8. The apparatus of claim 1, wherein the cannula comprises a polyurethane tube reinforced with a surrounding coil of nitinol.

9. The apparatus of claim 1, comprising a percutaneous ventricular assist device comprising the cannula, and comprising at least one pump located within the cannula.

10. The apparatus of claim 1, wherein the cannula has a shape closely matched to the anatomy of at least 80%, at least 85%, at least 90% or at least 95% of the adult human population.

11. A method comprising:
forming a cannula as recited in claim 1.

12. A method comprising:
implanting the apparatus of claim 1 in a human heart.

13. The apparatus of claim 1, wherein the cannula further comprises an extension that extends the cannula non-hydraulically beyond the outflow port.

14. The apparatus of claim 13, wherein the extension is flexible.

15. The apparatus of claim 13, wherein the extension comprises a pigtail tip.

16. The apparatus of claim 1, wherein the cannula is configured for percutaneous delivery.

17. A method comprising:
receiving medical image data corresponding the anatomy of the right ventricle of each of a plurality of human subjects;
processing the medical image data to determine landmark information indicative of the position of a plurality of anatomical landmarks, said landmarks including an inferior vena cava (IVC), right atrium (RA), tricuspid valve (TV), pulmonary valve (PV) and pulmonary artery (PA);
generating a cannula design based on the landmark information; and
fabricating a cannula comprising a shape memory material configured to provide the cannula with a shape based on the cannula design,
wherein the cannula design includes:
an outflow port configured to be located proximal the PA;
an inflow port configured to be located proximal the IVC;
a primary section corresponding to the path from a diaphragm fibrous ring in the IVC to the IVC to RA transition (IVC-RA), extending in a first direction;
a secondary section corresponding to the path from the IVC-RA to the TV, extending in a second direction different to the first direction;
a tertiary section corresponding to the path from the TV to the PV, extending in a third direction different from the first and second directions; and
a quaternary section corresponding to the path between the PV and the left branch of the PA, extending in a fourth direction, different from the first, second and third directions,
wherein:
the primary section extends from a point A to a point B and includes the inflow port proximal point A;
the secondary section extends from said point B to a point C;
the tertiary section extends from said point C to a point D; and
the quaternary section extends from said point D to a point E, having the outflow port proximal said point E;
wherein:
the primary, secondary and tertiary sections lie substantially in a first plane containing said points A, B, and C; and
the quaternary section lies substantially in a second plane containing points C, D, and E, the second plane being oriented to the first plane at an angle of about 30 degrees.

18. The method of claim 17, wherein the information indicative of the position of the IVC, RA, TV, PV and PA comprises:
a length and an angle between the IVC and the RA;
a length and an angle between the RA and the TV;
a length and an angle between the TV and PV; and
a length and an angle between the PV and PA.

19. The method of claim 17, wherein the cannula has a shape closely matched to the anatomy of at least 80%, at least 85%, at least 90% or at least 95% of the adult human population.

20. A product comprising:
a cannula fabricated using the method of claim 17; and
a pump configurable to pump blood entering the inflow port.

21. The product of claim 20, wherein the pump is enclosed within the cannula.

22. The method of claim 17, wherein the cannula design includes an extension that extends the cannula non-hydraulically beyond the outflow port.

23. The method of claim 17, wherein the cannula is configured for percutaneous delivery.

* * * * *